United States Patent
Omoda (10) Patent No.: US 8,481,987 B2
(45) Date of Patent: Jul. 9, 2013

(54) SENSOR INCLUDING A PHOTOCATALYST

(75) Inventor: Ryo Omoda, Kyoto (JP)

(73) Assignee: Empire Technology Development LLC, Wilmington, DE (US)

( * ) Notice: Subject to any disclaimer, the term of this patent is extended or adjusted under 35 U.S.C. 154(b) by 354 days.

(21) Appl. No.: 12/993,641

(22) PCT Filed: Jun. 18, 2010

(86) PCT No.: PCT/US2010/039245
§ 371 (c)(1),
(2), (4) Date: Nov. 19, 2010

(87) PCT Pub. No.: WO2011/159318
PCT Pub. Date: Dec. 22, 2011

(65) Prior Publication Data
US 2011/0308303 A1    Dec. 22, 2011

(51) Int. Cl.
*G01N 21/15* (2006.01)
*G01N 21/64* (2006.01)

(52) U.S. Cl.
USPC ............................... 250/573; 73/53.01

(58) Field of Classification Search
USPC ............................... 250/573; 73/53.01
See application file for complete search history.

(56) References Cited

U.S. PATENT DOCUMENTS

| | | | |
|---|---|---|---|
| 5,673,341 A * | 9/1997 | Takesue et al. | 385/12 |
| 6,217,999 B1 | 4/2001 | Zhang et al. | |
| 6,576,589 B1 | 6/2003 | Na et al. | |
| 2006/0111460 A1 | 5/2006 | Wakamura et al. | |
| 2009/0056157 A1 * | 3/2009 | Aoki | 33/503 |
| 2010/0044630 A1 | 2/2010 | Kang et al. | |

FOREIGN PATENT DOCUMENTS

| | | |
|---|---|---|
| GB | 2391307 | 2/2004 |
| JP | 10-281979 | 10/1998 |
| JP | 2003-344141 | 12/2003 |
| JP | 2008-088436 | 4/2008 |
| JP | 2009-061426 | 3/2009 |
| JP | 2009-150747 | 7/2009 |

OTHER PUBLICATIONS

Paz, Y. et al "Photooxidative self-cleaning transparent titanium dioxide films on glass," Journal of Materials Research 10 (11) 1995, pp. 2842-2848.

Watanabe, T. et al, "Photocatalytic activity and photoinduced hydrophilicity of titanium dioxide coated glass," Thin Solid Films 351 (1-2) 1999, pp. 260-263.

O'Regan, B. et al., "A low-cost, high-efficiency solar cell based on dye-sensitized colloidal TiO2 films," Nature 353 (6346) 1991, pp. 737-740.

James L. Gole, et al "Highly Efficient Formation of Visible Light Tunable TiO2-xNx Photocatalysts and Their Transformation at the Nanoscale," The Journal of Physical Chemistry B 2004 108 (4), 1230-1240.

(Continued)

*Primary Examiner* — Tony Ko
(74) *Attorney, Agent, or Firm* — Workman Nydegger (57) ABSTRACT

Devices and methods for degrading contaminants that may foul a sensor. A photocatalyst associated with the sensor is capable of interacting with a light source to prevent contamination of the sensor and/or to facilitate decontamination of the sensor by contaminants such as, but not limited to, organic compounds, volatile organic compounds (VOCs), organometallic compounds, soot, organic matter, bacteria, algae, eggs of aquatic organisms, planktonic larvae, and the like.

20 Claims, 4 Drawing Sheets

OTHER PUBLICATIONS

Masaaki Kitano, et al "Preparation of Visible Light-responsive $TiO_2$ Thin Film Photocatalysts by an RF Magnetron Sputtering Deposition Method and Their Photocatalytic Reactivity", Chemistry Letters vol. 34, No. 4 (2005).

M. Matsuoka, et al "Photocatalytic Water Splitting on Visible Light-responsive TiO2 Thin Films Prepared by a RF Magnetron Sputtering Deposition Method" Topics in Catalysis, vol. 35, Nos. 3-4, Jul. 2005, pp. 305-310.

Chen Shifu, et al "The preparation of coupled SnO2/TiO2 photocatalyst by ball milling" Materials Chemistry and Physics, vol. 98, Issue 1, Jul. 1, 2006, pp. 116-120.

Chao-Yin Kuo "Enhancement of photocatalytic activity in UV-illuminated tin dioxode/aluminum oxide system in aqueous 4-nitrophenol" Reaction Kinetics and Catalysis Letters, vol. 92, No. 2, Dec. 2007, pp. 337-343.

Q. Li, et al "Enhanced visible-light-induced photocatalytic disinfection of E. coli by carbon-sensitized nitrogen-doped titanium oxide", Environmental Science & Technology 2007 41 (14), pp. 5050-5056.

Pinggui Wu, et al "Visible-light-induced photocatalytic inactivation of bacteria by composite photocatalysts of palladium oxide and nitrogen-doped titanium oxide," Applied Catalysis B: Environmental, vol. 88, Issues 3-4, May 20, 2009, pp. 576-581.

University of Illinois at Urbana-Champaign "New visible light photocatalyst kills bacteria, even after light turned off" Published online by ScienceDirect: Tuesday, Jan. 19, 2010—12:16 in Physics & Chemistry [http://esciencenews.com/articles/2010/01/19/new.visible.light. photocatalyst.kills.bacteria.even.after.light.turned].

National Institute of Advanced Industrial Science and Technology (AIST) "Development of a Visible Light Responsive Photocatalyst using Tungsten Oxide under Indoor Lighting : Complete oxidative decomposition of various volatile organic compounds under visible light" AIST press release of Jul. 9, 2008 [online: http://www.aist.go.jp/aist_e/latest_research/2008/20080806/20080806.html#pagetop].

National Institute of Advanced Industrial Science and Technology (AIST) "Successful Synthesis of Tungsten Oxide Nanotubes by a Simple Method: Expected to be used as a visible-light-driven photocatalyst for indoor applications" AIST press release of Aug. 4, 2008 [online: http://www.aist.go.jp/aist_e/latest_research/2008/20080911/20080911.html].

Akihiko Kudo, et al "Effect of lanthanide-doping into NaTaO3 photocatalysts for efficient water splitting," Chemical Physics Letters, vol. 331, Issues 5-6, Dec. 8, 2000, pp. 373-377.

Hyun Woo Kang, et al "Preparation of NaTaO3 by Spray Pyrolysis and Evaluation of Apparent Photocatalytic Activity for Hydrogen Production from Water" International Journal of Photoenergy, vol. 2008 (2008), Article ID 519643, 8 pages.

Andrew Mills, et al "Spectral and photocatalytic characteristics of TiO2 CVD films on Quartz" Photochem. Photobiol. Sci., 2002, 1, pp. 865-868.

Nor Hafizah, et al "Nanosized TiO2 Photocatalyst Powder via Sol-Gel Method: Effect of Hydrolysis Degree on Powder Properties" International Journal of Photoenergy, vol. 2009 (2009), Article ID 962783, 8 pages.

Masaaki Kitano, et al "Preparation of Visible Light-responsive TiO2 Thin Film Photocatalysts by an RF Magnetron Sputtering Deposition Method and Their Photocatalytic Reactivity" Chemistry Letters vol. 34, No. 4 (2005), pp. 616-617.

International Search Report for International Application No. PCT/US2010/039245, European Patent Office, The Hague, Netherlands, mailed on Jul. 29, 2010.

* cited by examiner

SENSOR INCLUDING A PHOTOCATALYST

BACKGROUND

Photocatalysts have garnered significant attention not only for their potential use in the production of hydrogen and/or oxygen from water, but also in the treatment of waste materials and purification of air. Photocatalysts are frequently formed from semiconductors or from organometallic complexes, such as chlorophyll. Of the two, semiconductors are generally favored owing in part to their chemical stability, low cost of production, broad energy bandgaps, and the ease with which they can be handled.

Semiconductor photocatalysis is initiated by absorption of a photon of light having a wavelength of sufficient energy that is unique to the particular photocatalyst. Photon absorption creates separated electrons and holes across an energy bandgap. The strongly reducing electrons and the strongly oxidizing holes, generated by the optical excitation, can be coupled to reactions that can degrade environmental contaminants, split water for hydrogen production, and the like.

SUMMARY

Devices and methods are disclosed for degrading contaminants that may foul a sensor. During long-term monitoring (e.g., environmental monitoring), a typical sensor may become contaminated with or fouled by one or more of organic compounds, volatile organic compounds (VOCs), organometallic compounds, soot, organic matter, bacteria, algae, eggs of aquatic organisms, planktonic larvae, and the like. A photocatalyst associated with the sensor is capable of interacting with a light source to degrade contaminants to prevent contamination of the sensor and/or to facilitate decontamination of the sensor.

In one embodiment, a device is disclosed that includes a sensor and a photocatalyst associated with the sensor. The photocatalyst is configured to degrade materials that can foul the sensor to prevent contamination of the sensor and/or to facilitate decontamination of the sensor. In one aspect, the sensor may be configured to detect and/or monitor one or more of temperature, pH, conductivity, dielectric constant, salinity, turbidity, total suspended solids (TSS), total dissolved solids (TDS), biological oxygen demand (BOD), and chemical oxygen demand (COD). Suitable examples of photocatalysts that may be associated with the device include, but are not limited to, $TiO_2$, vis-$TiO_2$, $SnO_2/TiO_2$, $SnO_2/Al_2O_3$, TiON, TiON/PdO, $TiO_2/WO_3$, Pd—$WO_3$, CuO—$WO_3$, Pt—$WO_3$, $NaTaO_3$, $TiO_{2-x}N_x$, and combinations thereof.

In another embodiment, a device includes a sensor having a sensor portion, a light source associated with the device, and a photocatalyst associated with at least the sensor portion. Similar to the previous embodiment, the photocatalyst associated with at least the sensor portion is configured to degrade materials that can foul the sensor portion to prevent contamination of the sensor portion and/or to facilitate decontamination of the sensor portion.

In one aspect, the light source is configured to emit a wavelength of light selected to activate the photocatalyst. In another aspect, the light source is configured to emit UV light, visible light, or a combination thereof. In another aspect, the light source is selected from the group consisting of lamps, lasers, LEDs, other types of lights, and combinations thereof.

In yet another embodiment, a method is disclosed. The method includes steps of providing a sensor, associating a photocatalyst with the sensor, and activating the photocatalyst with a light source to prevent contamination of the sensor and/or to decontaminate the sensor. In one aspect, the light source can be sunlight or an artificial light source. In another aspect, the light source can be active at essentially all times or the light source can be activated for selected intervals for prevention of contamination and/or decontamination of the sensor.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Devices and methods are disclosed for degrading organic contaminants that may foul, contaminate, or degrade the performance of a sensor. Sensors can be placed in a number of environments for monitoring water quality, air quality, soil moisture content, salt content in soil or water, industrial processes, and the like. However, monitoring environments may include a variety of contaminants that can foul the sensor over the short- or long-term. The devices disclosed herein include a photocatalyst that is associated with the sensor that is capable of interacting with a light source to degrade many types of contaminants to prevent contamination of the sensor and/or to facilitate decontamination of the sensor.

I. Devices that Include a Photocatalyst

In one embodiment, a device is disclosed. The device includes a sensor and a photocatalyst that is associated with the sensor. A variety of sensors are known for monitoring properties such as, but not limited to, water quality, air quality, soil moisture content, salt content in soil or water, temperature, and the like. As such, in one aspect, the sensor may be configured to detect and/or monitor one or more of temperature, pH, conductivity, dielectric constant, salinity, turbidity, total suspended solids (TSS), total dissolved solids (TDS), biological oxygen demand (BOD), and chemical oxygen demand (COD). Sensors can also be configured to monitor/detect one or more of ammonium, barium, bromide, cadmium, calcium, chloride, copper, cyanide, fluoride, iodide, lead, mercury, nitrate, nitrite, perchlorate, potassium, sodium, silver, sulphide, sulfide, thiocyanate, sulphate, oxidation-reduction potential (ORP), dissolved oxygen (DO), and the like.

Many sensors are based on electrodes that are configured for monitoring a selected property of an environment. For instance, sensors are available in the market for monitoring salinity, soil moisture, and the like based on measurements of the conductivity and/or dielectric constant of the medium (i.e., soil) surrounding the sensor. The dielectric constant of water is quite high at about 80. In contrast, materials such as soil typically only have a dielectric constant of about 4. One can appreciate, therefore, that changes in the water content of soil can cause relatively large changes in the dielectric constant that can be monitored by the sensor.

Another typical type of electrode is the pH electrode. Most often used pH electrodes are glass electrodes. A typical pH electrode includes a glass tube with a small glass bubble on its end, and a silver/silver chloride electrode in the tube. The tube of the electrode is usually filled with a buffered solution of chlorides in which the silver electrode is immersed.

The active part of the electrode is the glass bubble. The surface of the glass bubble is protonated by both internal and external solutions, which typically results in a charge differential that is measured and converted to a pH reading. The majority of pH electrodes available commercially are so-called "combination electrodes" that include a glass H+ ion sensitive electrode and an additional reference electrode in a single housing.

Ion selective electrodes such as those configured to detect one or more of ammonium, barium, bromide, cadmium, calcium, chloride, copper, cyanide, fluoride, iodide, lead, mercury, nitrate, nitrite, perchlorate, potassium, sodium, silver, sulphide, sulfide, thiocyanate, sulphate, oxidation-reduction potential (ORP), dissolved oxygen (DO), and the like work similarly to pH electrodes. In ion selective electrodes, the glass bulb is typically replaced with an ion-specific membrane. Interaction of the specific ion with the ion selective membrane produces a potential difference that can be detected and converted to a concentration measurement for the ion under examination. Ion-selective electrodes are used in biochemical and biophysical research, where measurements of ionic concentration in an aqueous solution are required, usually on a real time basis.

A variety of sensors are also available in the market for monitoring turbidity, total suspended solids (TSS), total dissolved solids (TDS), biological oxygen demand (BOD), and chemical oxygen demand (COD). Additional discussion of water monitoring techniques and sensors can be found in "Standard Methods for the Examination of Water and Wastewater" (20th ed.) Clescerl, Leonore S. (Editor), Greenberg, Arnold E. (Editor), Eaton, Andrew D. (Editor), American Public Health Association, Washington, D.C. ISBN 0-87553-235-7, the entirety of which is incorporated herein by reference.

In one embodiment, the device disclosed herein is configured for insertion into a medium such as, but not limited to, a testable medium. Suitable examples of testable media include solid, porous media, liquids, gases, and combinations thereof. Additional suitable examples of testable media include at least one of soil, water, or air. In one embodiment, the sensors described herein can be installed for long-term monitoring of the testable media. For example, the sensor devices disclosed herein may be configured to be submerged in water for long-term monitoring of water quality.

Any one of the sensors described herein can become fouled by a number of potential contaminants while monitoring a testable medium. Suitable examples of potential contaminants that can foul a sensor include, but are not limited to organic compounds, volatile organic compounds (VOCs), organometallic compounds, soot, organic matter, bacteria, algae, eggs of aquatic organisms, planktonic larvae, and combinations thereof. For example, any one of or a combination of organic compounds, volatile organic compounds (VOCs), organometallic compounds, soot, organic matter may collect on the surface of a sensor and degrade the performance of the sensor. Living matter such as, but not limited to, bacteria, algae, eggs of aquatic organisms, planktonic larvae may likewise settle on a sensor or propagate on the surface of a sensor and degrade the performance of the sensor.

Suitable examples of photocatalysts that may be associated with the device include, but are not limited to, $TiO_2$, vis-$TiO_2$, $SnO_2/TiO_2$, $SnO_2/Al_2O_3$, TiON, TiON/PdO, $TiO_2/WO_3$, Pd—$WO_3$, CuO—$WO_3$, Pt—$WO_3$, $NaTaO_3$, $TiO_{2-x}N_x$, and combinations thereof.

When a photocatalyst absorbs a photon of light having sufficient energy, an electron can be excited. The resulting "hole/electron" pair is highly reactive and can be coupled to a variety of reactions that can degrade organic materials. This phenomenon is schematically illustrated in FIG. 1.

Figure 1:
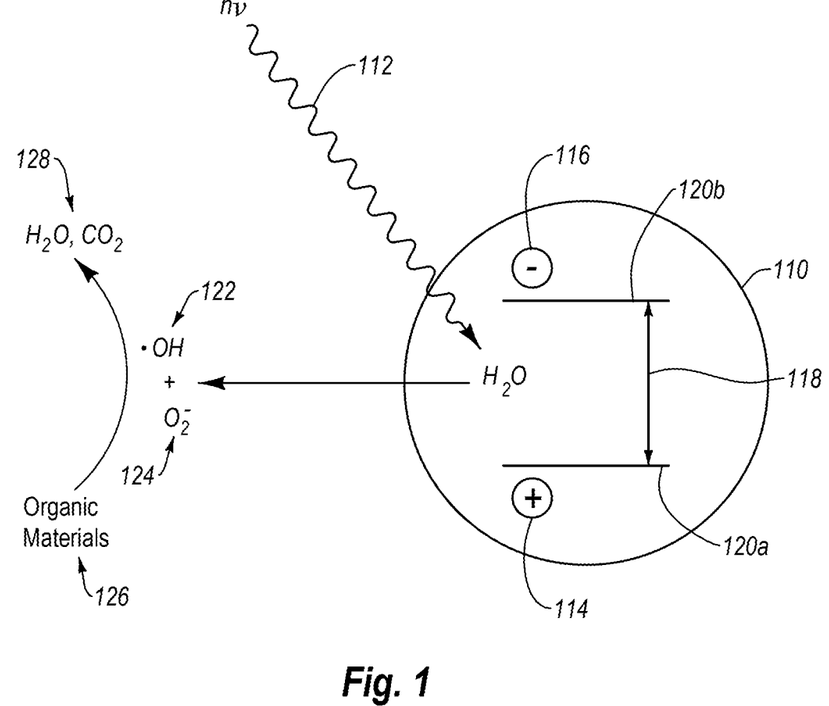
FIG. 1 schematically depicts the mechanism of photocatalytic degradation of organic material according to one embodiment of the present disclosure.

FIG. 1 shows a photocatalyst particle 100 being irradiated by a photon 112 with energy hv. When the photon 112 is absorbed by the photocatalyst 100, an electron is excited across the band-gap 118 from the valence band 120a to the conduction band 120b. This creates a negatively charged electron 116 in the conduction band 120b and a positively charged hole 114 in the valence band 120a. The hole 114 is a powerful oxidizing agent. For instance, the hole 114 can oxidize water to create hydroxyl radicals (·OH) 122. Hydroxyl radicals can react oxygen to form superoxide anion ($O_2^-$) 124. Hydroxyl radical 122 and superoxide anion 124 can degrade a wide variety organic materials 126 to produce $H_2O$ and $CO_2$ 128. The holes 114 can also oxidize organic materials 126 directly. Photocatalysts are also known to greatly increase the hydrophilicity of surfaces such as, but not limited to, glass, which can allow surfaces to be kept clean and free of contaminants by the action of water alone. Further discussion of this phenomenon can be found in "Photooxidative self-cleaning transparent titanium dioxide films on glass," Journal of Materials Research 10 (11) 1995 2842-2848 Paz, Y. et al and "Photocatalytic activity and photoinduced hydrophilicity of titanium dioxide coated glass," Thin Solid Films 351 (1-2) 1999 260-263 Watanabe, T. et al, the entirties of which are incorporated herein by reference. As such, photocatalysts can be used to prevent or reverse fouling of a sensor by organic materials.

One example of a photocatalyst that can be used with the devices and methods disclosed herein is titanium dioxide ($TiO_2$). Of the photocatalysts discussed herein, $TiO_2$ is the most common and best known. $TiO_2$ is the naturally occurring oxide of titanium. $TiO_2$ is noteworthy for its wide range of applications, from paint to sunscreen to food coloring.

There are three common crystal forms of $TiO_2$—rutile, brookite, and anatase. The rutile and anatase forms of $TiO_2$ are the known to be photocatalytically active, with the anatase form being the more active of the two. The anatase form of $TiO_2$ is activated by ultraviolet (UV) light having a wavelength of about 388 nm or shorter. Recently it has been found that titanium dioxide, when spiked with nitrogen ions or doped with metal oxide like tungsten trioxide (referred to generally herein as vis-$TiO_2$), is also a photocatalyst under either visible or UV light.

When $TiO_2$ absorbs light it produces reactive species that can react with and degrade organic materials. Titanium dioxide is thus added to paints, cements, windows, tiles, or other products for its sterilizing, deodorizing and anti-fouling properties and is used as a hydrolysis catalyst. Additional discussion of $TiO_2$, its photocatalytic properties, and methods for its preparation can be found, for example, in U.S. Pat. No. 6,576,589 and "A low-cost, high-efficiency solar cell based on dye-sensitized colloidal TiO2 films," Nature 353 (6346) 1991 737-740, O'Regan, B. et al., the entireties of which are incorporated herein by reference.

Additional photocatalysts that can be used with the devices and methods discussed herein include, but are not limited to, vis-$TiO_2$, $SnO_2/TiO_2$, $SnO_2/Al_2O_3$, TiON, TiON/PdO, $TiO_2/WO_3$, Pd—$WO_3$, CuO—$WO_3$, Pt—$WO_3$, $NaTaO_3$, $TiO_{2-x}N_x$, and combinations thereof. In contrast to $TiO_2$, many of these photocatalysts can be activated by visible light of various wavelengths (i.e., wavelengths of about 380 nm to about 800 nm), which may be advantageous in situations where there is little available natural UV light. In addition, artificial light sources that produce visible light are generally less specialized and generally consume less energy than sources designed to produce UV.

For example, $TiO_{2-x}N_x$ is a photocatalyst in which some of the oxygen in $TiO_2$ is displaced by nitrogen atoms. $TiO_{2-x}N_x$ is activated by light having a wavelength of less than about 500 nm, which promises a wide range of applications as it covers the main peak of the solar irradiation energy (i.e., around 460 nm). In addition, there are excellent artificial light sources that cover this range including recently developed light-emitting indium gallium nitride diodes that have a peak emission wavelength around 390 to 420 nm. Additional discussion of $TiO_{2-x}N_x$ can be found in U.S. Pat. Pub. No. 2010/0044630 and "Highly Efficient Formation of Visible Light Tunable $TiO_{2-x}N_x$ Photocatalysts and Their Transformation at the Nanoscale," James L. Gole and, John D. Stout, Clemens Burda, Yongbing Lou, and, Xiaobo Chen, The Journal of Physical Chemistry B 2004 108 (4), 1230-1240, the entireties of which are incorporated herein by reference.

Visible light $TiO_2$ (vis-$TiO_2$) can be activated by light having a wavelength of about 500 nm to about 600 nm, depending on how the catalyst is prepared. Additional discussion of vis-$TiO_2$ can be found in "Preparation of Visible Light-responsive $TiO_2$ Thin Film Photocatalysts by an RF Magnetron Sputtering Deposition Method and Their Photocatalytic Reactivity," Masaaki Kitano, Masato Takeuchi, Masaya Matsuoka, John M. Thomas, and Masakazu Anpo, Chemistry Letters Vol. 34, No. 4 (2005), and "Photocatalytic Water Splitting on Visible Light-responsive $TiO_2$ Thin Films Prepared by a RF Magnetron Sputtering Deposition Method," M. Matsuoka, M. Kitano, M. Takeuchi, M. Anpo and J. M. Thomas, Topics in Catalysis, Volume 35, Numbers 3-4, July, 2005, Pages 305-310, the entireties of which are incorporated herein by reference.

The absorption characteristics of $SnO_2/TiO_2$ are similar to those of $TiO_2$, except that $SnO_2$ stabilizes the excited state of $TiO_2$ and the mixed material is more catalytically active that $TiO_2$ alone. Additional discussion of $SnO_2/TiO_2$ can be found in "The preparation of coupled SnO2/$TiO_2$ photocatalyst by ball milling," Chen Shifu, Chen Lei, Gao Shen, Cao Gengyu, Materials Chemistry and Physics, Volume 98, Issue 1, 1 Jul. 2006, Pages 116-120, the entirety of which is incorporated herein by reference.

The absorption characteristics of $SnO_2/Al_2O_3$ are similar to those of $TiO_2$. The behavior of $SnO_2/Al_2O_3$ is also similar to that of $SnO_2/TiO_2$ in that the mixed material is more photochemically active than either component alone. Additional discussion of $SnO_2/Al_2O_3$ can be found in "Enhancement of photocatalytic activity in UV-illuminated tin dioxide/aluminum oxide system in aqueous 4-nitrophenol," Chao-Yin Kuo, Reaction Kinetics and Catalysis Letters, Volume 92, Number 2/December, 2007, Pages 337-343, the entirety of which is incorporated herein by reference.

TiON can be activated by visible light having a wavelength of about 400 nm to about 800 making it a true visible light photocatalyst. Additional discussion of TiON can be found in "Enhanced Visible-Light-Induced Photocatalytic Disinfection of E. coli by Carbon-Sensitized Nitrogen-Doped Titanium Oxide," Qi Li, Rongcai Xie, Yin Wai Li, Eric A. Mintz, and, Jian Ku Shang, Environmental Science & Technology 2007 41 (14), 5050-5056), the entirety of which is incorporated herein by reference.

Likewise, TiON/PdO can be activated by visible light having a wavelength of about 400 nm to about 800 making it a true visible light photocatalyst. Additional discussion of TiON/PdO can be found in "Visible-light-induced photocatalytic inactivation of bacteria by composite photocatalysts of palladium oxide and nitrogen-doped titanium oxide," Pinggui Wu, Rongcai Xie, James A. Imlay, Jian Ku Shang, Applied Catalysis B: Environmental, Volume 88, Issues 3-4, 20 May 2009, Pages 576-581, and University of Illinois at Urbana-Champaign (Jan. 20, 2010) "New visible light photocatalyst kills bacteria, even after light turned off," ScienceDaily (published online at the ScienceDaily website), the entireties of which are incorporated herein by reference.

$TiO_2/WO_3$, Pd—$WO_3$, CuO—$WO_3$, Pt—$WO_3$ can be activated by light having a wavelength of about 400 nm to about 800 nm. Additional discussion of $TiO_2/WO_3$, Pd—$WO_3$, CuO—$WO_3$, Pt—$WO_3$, can be found in JP 2009-61426; "Development of a Visible Light Responsive Photocatalyst using Tungsten Oxide under Indoor Lighting, Complete oxidative decomposition of various volatile organic compounds under visible light" (published online at the National Institute of Advanced Industrial Science and Technology (AIST) website); and "Successful Synthesis of Tungsten Oxide Nanotubes by a Simple Method, Expected to be used as a visible-light-driven photocatalyst for indoor applications," (published online at the AIST website), the entireties of which are incorporated herein by reference.

$NaTaO_3$ can be activated by light having a wavelength of about 250 nm to about 300 nm. Additional discussion of $NaTaO_3$ can be found in "Effect of lanthanide-doping into $NaTaO_3$ photocatalysts for efficient water splitting," Akihiko Kudo, Hideki Kato, Chemical Physics Letters, Volume 331, Issues 5-6, 8 Dec. 2000, Pages 373-377, "Preparation of $NaTaO_3$ by Spray Pyrolysis and Evaluation of Apparent Photocatalytic Activity for Hydrogen Production from Water," Hyun Woo Kang, Eun-Jung Kim, and Seung Bin Park, International Journal of Photoenergy, Volume 2008 (2008), Article ID 519643, 8 pages, the entireties of which are incorporated herein by reference.

In one embodiment, the surface of the sensor that the photocatalyst is applied to can be formed from a glass material such as, but not limited to, borosilicate glass, soda glass, or quartz, a metal material such as, but not limited to, stainless steel, aluminum, copper, and various metal alloys, and plastic materials such as, but not limited to, polycarbonate, polystyrene, nylon, and polyethylene. Photocatalyst can be applied to the surface of a sensor or a cover that is situated over a sensor by any conventional technique known in the art. Conventional techniques include, but are not limited to, chemical vapor deposition, spray coating, sputtering, and sol-gel methods. Further discussion of these deposition techniques can be found in "Spectral and Photocatalytic Characteristics of $TiO_2$ CVD Films on Quartz," Mills et al., Photochem. Photobiol. Sci., 2002, 1, 865-868; "Nanosized $TiO_2$ Photocatalyst Powder via Sol-Gel Method: Effect of Hydrolysis Degree on Powder Properties," Hafizah et al., International Journal of Photoenergy, Volume 2009, Article ID 962783, 8 pages; "Preparation of Visible Light-responsive $TiO_2$ Thin Film Photocatalysts by an RF Magnetron Sputtering Deposition Method and Their Photocatalytic Reactivity," Kitano et al., Chemistry Letters (2005) vol. 34, pp. 616-617; and "Preparation of $NaTaO_3$ by Spray Pyrolysis and Evaluation of Apparent Photocatalytic Activity for Hydrogen Production from Water," Kang et al., International Journal of Photoenergy, Volume 2008, Article ID 519643, 8 pages, the entireties of which are incorporated herein by reference.

In some instances, photocatalysts have been known to react with substrates that they are attached to. For example, the reactive species (e.g., hydroxyl radicals) that allow the photocatalyst to degrade organic materials that settle on a surface can also degrade the surface if the surface (e.g., plastic) includes materials that are susceptible to attack by the reactive species. In one embodiment, photocatalyst-induced degradation of susceptible substrates can be prevented by inclusion of a protective layer that keeps the photocatalyst from directly contacting the substrate. For example, apatite can be used as a protective layer. In another embodiment, the photocatalyst can be encapsulated in a protective layer. Further discussion of these techniques can be found in JP2008-088436 and U.S. Pat. No. 6,217,999, the entireties of which are incorporated herein by reference.

Figure 2:
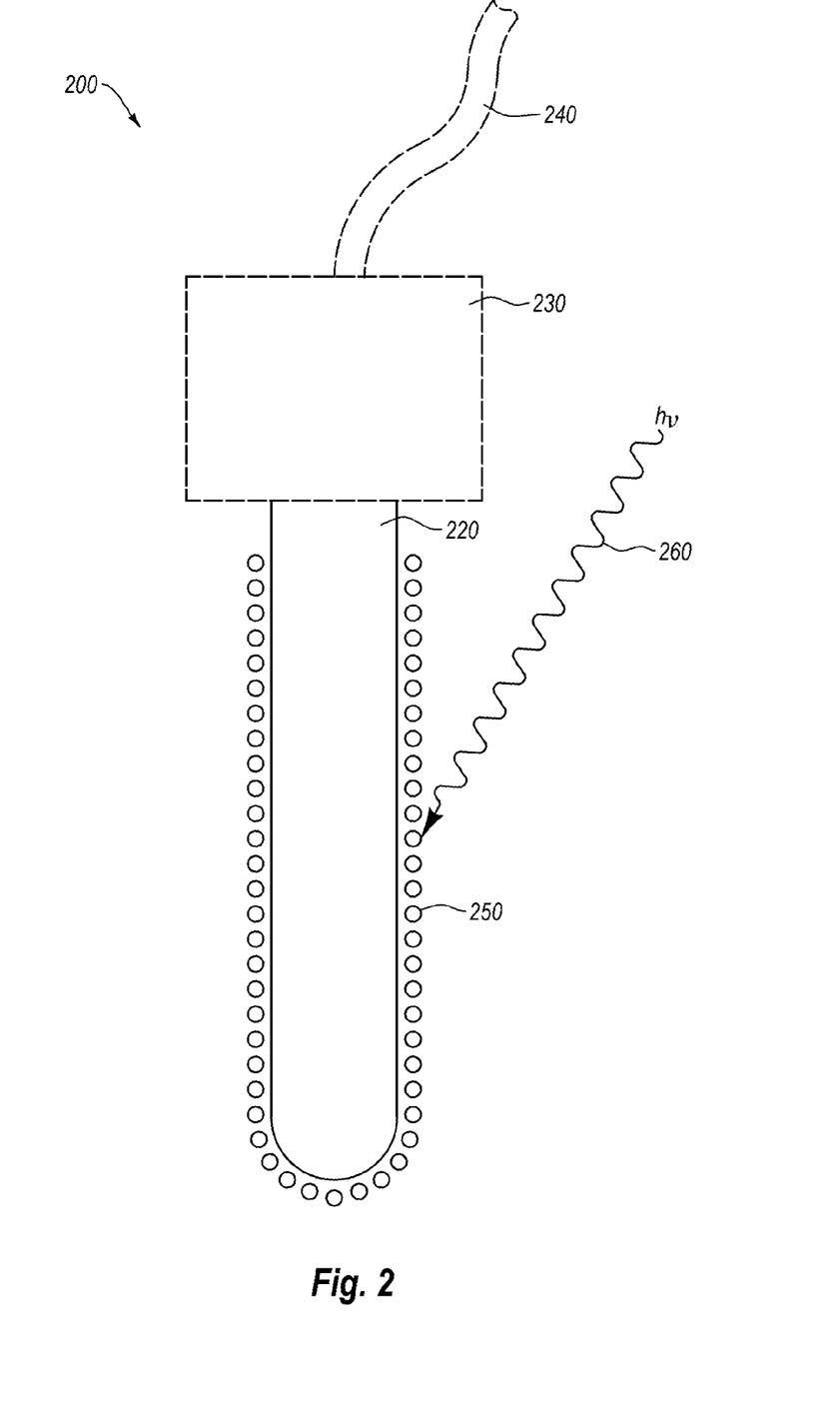
FIG. 2 depicts an illustrative embodiment of a device that includes sensor and a photocatalyst according to one embodiment of the present disclosure.

Referring now to FIG. 2, an illustrative embodiment of a device 200 that includes a sensor and a photocatalyst is shown. The device 200 includes a sensor portion 220 and a photocatalyst layer 250 on the sensor section 220. As shown in FIG. 2, the device 200 may optionally include a housing 230 that may be configured to house various electronic components associated with the sensor portion 220. In another embodiment (not shown), the sensor portion 220 may be configured to include all of the various electronic components needed to operate the device. Also as shown in FIG. 2, the device 200 may optionally include an electrical connection 240 that may be configured to provide electrical power to the device 200 and/or to transmit data to and from the device 200. In additional embodiments (not shown), the device 200 may be powered by a battery or a solar cell. Additionally, regardless of the power source, the device 200 may be configured to receive and transmit data wirelessly.

As discussed in greater detail above, the sensor portion 220 may be configured to detect and/or monitor one or more of temperature, pH, one or more selected ions (e.g., sodium, nitrate, nitrite, and the like), conductivity, dielectric constant, salinity, turbidity, total suspended solids (TSS), total dissolved solids (TDS), biological oxygen demand (BOD), and chemical oxygen demand (COD).

As discussed in greater detail above, the photocatalyst layer 250 on the device 200 is capable of interacting with light to prevent contamination of the sensor portion 220 or to decontaminate the sensor portion 220. This is schematically illustrated by incident photon 260. As was explained in detail with respect to FIG. 1, the photon 260 can interact with the photocatalyst 250 to produce reactive species that can degrade a variety of organic contaminants that may otherwise foul the sensor portion 220. It is not expected that the photocatalyst layer 250 will interfere with the function of the device 200 so long as the photocatalyst layer 250 is applied such that it does not block the sensor portion 220. Nevertheless, the products of degradation can interfere with some measurements in some instances. For example, $CO_2$ may interfere with pH measurements. In such cases, it may be necessary to deactivate the decontamination system (e.g., by blocking the light source 260) during measurement. In cases where the light source 260 is sunlight, measurements could be conducted during the night.

Essentially any suitable light source may be the source of photon 260. For example, in environments where the device 200 is impinged upon by ambient light, the source of photon 260 may be sunlight and/or an artificial light source such as, but not limited to, indoor lighting such as from fluorescent or incandescent lighting. Sunlight includes essentially all wavelengths needed to stimulate any of the photocatalysts discussed herein, whereas most artificial lighting is limited to the visible spectrum (i.e., about 400 nm to about 800 nm). Nevertheless, artificial light sources can be provided for stimulating essentially any of the photocatalysts discussed herein.

In environments where the sensor is not exposed to ambient light, such as underground, in deep water, in substantially opaque media (e.g., water with a large percentage of suspended solids), and in a closed environment (e.g., inside a pipe), the device may include its own light source. This is illustrated in FIGS. 3 and 4.

Figure 3:
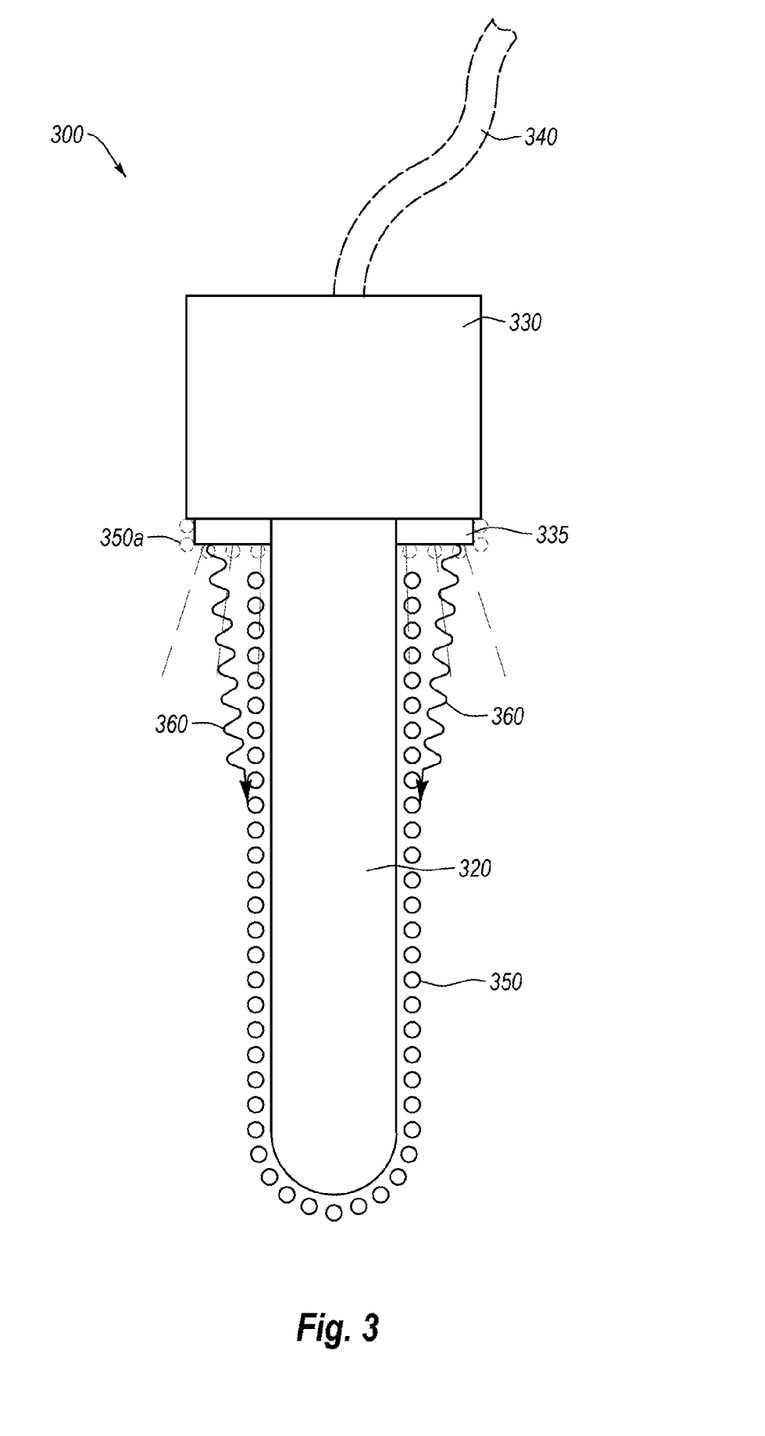
FIG. 3 depicts an illustrative embodiment of a device that includes sensor, a photocatalyst, and a light source configured to activate the photocatalyst according to one embodiment of the present disclosure.
Figure 4:
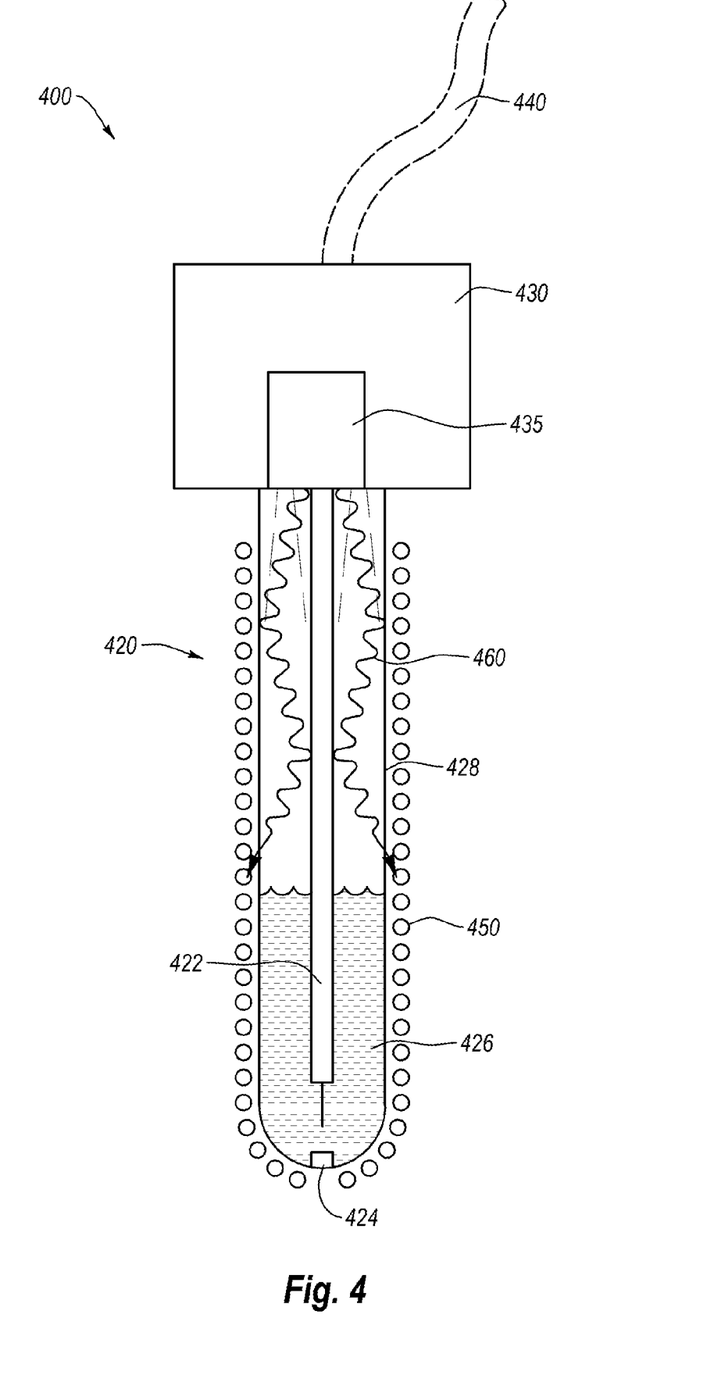
FIG. 4 depicts an illustrative embodiment of a device that includes sensor, a photocatalyst, and an internal light source configured to activate the photocatalyst according to one embodiment of the present disclosure.

FIG. 3 illustrates another embodiment of a device 300. Device 300 includes a sensor portion 320, a housing 330, and a photocatalyst layer 350 on the sensor section 320. Also as shown in FIG. 3, the device 300 may optionally include an electrical connection 340 that may be configured to provide electrical power to the device 300 and/or to transmit data to and from the device 300. In additional embodiments (not shown), the device 300 may be powered by a battery or a solar cell. Additionally, regardless of the power source, the device 300 may also be configured to receive and transmit data wirelessly.

As shown in FIG. 3, the device 300 additionally includes a light source 335 that can be configured to emit photons 360 that can stimulate the photocatalyst 350. In the illustrated embodiment, the light source 335 includes an optional layer of photocatalyst 350a. In some embodiments, the photocatalyst 350a may be included on the light source 335 to prevent the same organic contaminants that can foul the sensor portion 320 from obscuring the light source 335. In the illustrated embodiment the light source is situated in the housing. One will appreciate, however, that the light source 335 can be associated with essentially any portion of the device 300. Additionally, the light source 335 can be detachable from the device 300 and/or the light source 335 can be configured to be retrofitted onto a device 300 such as by snapping onto the housing 330.

Suitable examples of lights that can be included in light source 335 include, but are not limited to, lamps (e.g., incandescent lamps, fluorescent lamps, gas discharge lamps, etc), lasers, LEDs, and combinations thereof. The light source 335 can be configured to emit essentially any wavelength of light. For example, the light source 335 can be selected or configured to emit one or more wavelengths in a range from about 150 nm to about 800 nm. In a more specific example, the light source 335 can be selected or configured to emit one or more wavelengths in a range from about 330 nm to about 420 nm, about 350 nm to about 400 nm, about 380 nm to about 500 nm or about 390 nm to about 420 nm.

Referring now to FIG. 4, an illustrative embodiment of a device 400 that includes an internal light source 435 is illustrated. The device 400 may be a standard pH electrode on an ion selective as described above with a sensor section 420 includes an internal electrode 422 housed in an outer tube/body 428. The device 400 includes an outer tube/body 428 that is coated with a photocatalyst 450. The outer tube 428 includes an electrode section 420, an internal electrode 422, an internal electrode solution 426 and a junction 424 (e.g., a glass frit) that allows the internal electrode to sense the environment outside the outer tube 428. For example, the junction 424 can allow the internal solution 426 to equilibrate either partially or completely with a solution outside of the electrode. As shown, the light from the light source (e.g., photons 460) is reflected inside the outer tube to provide the sensor section 420 with sufficient light to stimulate the photocatalyst 450 for decomposition of contaminants.

The outer tube 428 can be made from any suitable material that is capable of transmitting the light 460 from the light source from the inside of the tube 428 to the photocatalyst 450. Suitable examples of materials from which the outer tube can be made include, but are not limited to, glass, plastics, and the like.

In one embodiment, the outer tube 428 can be integral to the device 400. In another embodiment, the outer tube 428 can be retrofitted on a device 400.

II. Methods for Decontaminating a Sensor

In one embodiment, a method is disclosed for decontaminating a sensor. The method includes steps of providing a sensor, associating a photocatalyst with the sensor, and activating the photocatalyst with a light source to prevent contamination of the sensor and/or to decontaminate the sensor. In one aspect, the light source can be sunlight or an artificial light source. In another aspect, the light source can be active at essentially all times or the light source can be activated for selected intervals for prevention of contamination and/or decontamination of the sensor. In yet another aspect, the light can have a narrow spectrum of wavelengths or a broad spectrum of wavelengths.

In one embodiment, the sensor provided is configured for sensing or detecting one or more of water quality, air quality, soil moisture content, salt content in soil or water, temperature, and the like. As such, in one aspect, the sensor may be configured to detect and/or monitor one or more of temperature, pH, conductivity, dielectric constant, salinity, turbidity, total suspended solids (TSS), total dissolved solids (TDS), biological oxygen demand (BOD), and chemical oxygen demand (COD). Sensors can also be configured to monitor/detect one or more of ammonium, barium, bromide, cadmium, calcium, chloride, copper, cyanide, fluoride, iodide, lead, mercury, nitrate, nitrite, perchlorate, potassium, sodium, silver, sulphide, sulfide, thiocyanate, sulphate, oxidation-reduction potential (ORP), dissolved oxygen (DO), and the like.

Any one of the sensors described herein can become fouled by a number of potential contaminants while monitoring a testable medium. Suitable examples of potential contaminants that can foul a sensor include, but are not limited to organic compounds, volatile organic compounds (VOCs), organometallic compounds, soot, organic matter, bacteria, algae, eggs of aquatic organisms, planktonic larvae, and combinations thereof. For example, any one of or a combination of organic compounds, volatile organic compounds (VOCs), organometallic compounds, soot, organic matter may collect on the surface of a sensor and degrade the performance of the sensor. Living matter such as, but not limited to, bacteria, algae, eggs of aquatic organisms, planktonic larvae may likewise settle on a sensor or propagate on the surface of a sensor and degrade the performance of the sensor.

Suitable examples of photocatalysts that may be associated with the device include, but are not limited to, $TiO_2$, vis-$TiO_2$, $SnO_2/TiO_2$, $SnO_2/Al_2O_3$, TiON, TiON/PdO, $TiO_2/WO_3$, Pd—$WO_3$, CuO—$WO_3$, Pt—$WO_3$, $NaTaO_3$, $TiO_{2-x}N_x$, and combinations thereof.

In one embodiment, the method can further include providing a light source configured to emit a wavelength of light capable of activating the photocatalyst. In one embodiment, the light source provided emits visible light, UV light, or a combination thereof. In one embodiment, the light source provided can include a natural light source (e.g., sunlight) or an artificial light source selected from the group consisting of lamps, lasers, LEDs, and combinations thereof.

In one embodiment, associating the photocatalyst with the sensor includes one or more of spray coating, chemical vapor deposition, a sol gel process, and chemical vapor deposition, sputter coating, and the like.

The present disclosure is not to be limited in terms of the particular examples described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth."

As used herein, the term "substantially" is used to mean to a great extent or degree. The term "substantially" is often used in conjunction with another term to describe the extent or degree of that term such as, but not limited to, angles, shapes, and states of being. For example, the term "substantially perpendicular" may be used to indicate some degree of leeway in an angular measurement. That is, an angle that is "substantially perpendicular" may be 90°, but angles such as 45°, 60°, 65°, 70°, 75°, 80°, 85°, 95°, 100°, 105°, 110°, 115°, 120°, 125°, 130, or 135° may also be considered to be "substantially perpendicular." Similarly, "substantially" may be used in conjunction with a shape term such as "substantially cylindrical" to indicate that the object referred to may have a circular profile or an ovoid profile. Likewise, a term describing a state of being such as the term "substantially closed," may be used to indicate that something is mostly closed or usually closed, but that it need not be 100% closed or always closed.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A water quality test device, the device comprising:
   a sensor adapted for testing water quality and having a sensor body adapted for emersion in water and at least partially transparent to UV light and/or visible light;
   a protective layer located on an outer surface of the sensor body and at least partially transparent to UV light and/or visible light; and
   a photocatalyst located on an outer surface of the protective layer so as to be associated with the sensor.

2. The device of claim 1, wherein the sensor is adapted to detect one or more of temperature, pH, conductivity, dielectric constant, salinity, turbidity, total suspended solids (TSS), total dissolved solids (TDS), biological oxygen demand (BOD), and chemical oxygen demand (COD).

3. The device of claim 1, wherein the photocatalyst is adapted to prevent contamination of the sensor and/or to facilitate decontamination of the sensor and/or to degrade one or more of organic compounds, volatile organic compounds (VOCs), organometallic compounds, soot, organic matter, bacteria, algae, eggs of aquatic organisms, planktonic larvae, and combinations thereof.

4. The device of claim 1, wherein the photocatalyst is selected from the group consisting of $TiO_2$, vis-$TiO_2$, $SnO_2$/$TiO_2$, $SnO_2$/$Al_2O_3$, TiON, TiON/PdO, $TiO_2$/$WO_3$, Pd—$WO_3$, CuO-$WO_3$, Pt—$WO_3$, $NaTaO_3$, $TiO_{2-x}N_x$, and combinations thereof.

5. The device of claim 1, wherein the protective layer includes apatite.

6. The device of claim 1, wherein the photocatalyst is partially encapsulated in the protective layer.

7. The device of claim 1, further comprising a light source selected to emit UV light and/or visible light that is enclosed by the sensor body and oriented to direct light from within the sensor body to the photocatalyst outside of the sensor body.

8. The device of claim 1, wherein the sensor body includes a glass or plastic material.

9. The device of claim 1, wherein the sensor body is adapted to be submerged in water for long-term monitoring of water quality.

10. The device of claim 9, wherein the photocatalyst is adapted to prevent contamination of the sensor by one or more of organic matter, bacteria, algae, eggs of aquatic organisms, planktonic larvae, and combinations thereof.

11. A water quality test device, the device comprising:
    a sensor adapted for testing water quality and having a sensor body adapted for emersion in water and at least partially transparent to UV light and/or visible light;
    a protective layer located on an outer surface of the sensor body and at least partially transparent to UV light and/or visible light;
    a photocatalyst located on an outer surface of the protective layer so as to be associated with the sensor; and
    a light source located within the sensor and enclosed by the sensor body and oriented to emit a wavelength of light that activates the photocatalyst from within the sensor body to the photocatalyst outside of the sensor body.

12. The device of claim 11, wherein the sensor is adapted to detect one or more of temperature, pH, conductivity, salinity, turbidity, total suspended solids (TSS), total dissolved solids (TDS), biological oxygen demand (BOD), and chemical oxygen demand (COD).

13. The device of claim 11, wherein the photocatalyst is adapted to prevent contamination of the sensor and/or to facilitate decontamination of the sensor and/or to degrade one or more of organic compounds, volatile organic compounds (VOCs), organometallic compounds, soot, organic matter, bacteria, algae, eggs of aquatic organisms, planktonic larvae, and combinations thereof.

14. The device of claim 11, wherein the photocatalyst is selected from the group consisting of $TiO_2$, vis-$TiO_2$, $SnO_2$/$TiO_2$, $SnO_2$/$Al_2O_3$, TiON, TiON/PdO, $TiO_2$/$WO_3$, Pd—$WO_3$, CuO-$WO_3$, Pt—$WO_3$, $NaTaO_3$, $TiO_{2-x}N_x$, and combinations thereof.

15. The device of claim 11, wherein the sensor body is adapted to be submerged in water for long-term monitoring of water quality.

16. The device of claim 15, wherein the photocatalyst is adapted to prevent contamination of the sensor portion and/or to facilitate decontamination of the sensor caused by one or more of organic matter, bacteria, algae, eggs of aquatic organisms, planktonic larvae, and combinations thereof.

17. A method for water quality testing, the method comprising:
    providing a sensor adapted for testing water quality, the sensor comprising:
        a sensor body adapted for emersion in water and at least partially transparent to UV light and/or visible light;
        a protective layer located on an outer surface of the sensor body and at least partially transparent to UV light and/or visible light; and
        a photocatalyst located on an outer surface of the protective layer so as to be associated with the sensor;
    inserting the sensor body, protective layer, and photocatalyst into water to be tested for water quality; and
    activating the photocatalyst with a light source to prevent contamination of the sensor and/or to decontaminate the sensor.

18. The method of claim 17, comprising detecting one or more of temperature, pH, conductivity, salinity, turbidity, total suspended solids (TSS), total dissolved solids (TDS), biological oxygen demand (BOD), and chemical oxygen demand (COD).

19. The method of claim 17, further comprising the sensor having the light source enclosed by the sensor body and oriented to emit a wavelength of light that activates the photocatalyst from within the sensor body to the photocatalyst outside of the sensor body.

20. The method of claim 17, further comprising submerging the sensor body in water for long-term monitoring of water quality and inhibiting contamination of the sensor body by one or more of organic matter, bacteria, algae, eggs of aquatic organisms, planktonic larvae, and combinations thereof.

* * * * *

UNITED STATES PATENT AND TRADEMARK OFFICE
CERTIFICATE OF CORRECTION

PATENT NO. : 8,481,987 B2  
APPLICATION NO. : 12/993641  
DATED : July 9, 2013  
INVENTOR(S) : Omoda Page 1 of 2

It is certified that error appears in the above-identified patent and that said Letters Patent is hereby corrected as shown below:

On the Title Page, in Item (56), under "OTHER PUBLICATIONS", in Column 2, Line 1, delete "Paz, Y. et al" and insert -- Paz, Y. et al., --, therefor.

On the Title Page, in Item (56), under "OTHER PUBLICATIONS", in Column 2, Line 4, delete "Watanabe, T. et al," and insert -- Watanabe, T. et al., --, therefor.

On the Title Page, in Item (56), under "OTHER PUBLICATIONS", in Column 2, Line 10, delete "James L. Gole, et al" and insert -- James L. Gole, et al., --, therefor.

Title Page 2, in Item (56), under "OTHER PUBLICATIONS", in Column 1, Lines 1-4, delete "Masaaki Kitano, et al "Preparation of Visible Light-responsive $TiO_2$ Thin Film Photocatalysts by an RF Magnetron Sputtering Deposition Method and Their Photocatalytic Reactivity", Chemistry Letters vol. 34, No. 4 (2005).".

Title Page 2, in Item (56), under "OTHER PUBLICATIONS", in Column 1, Line 5, delete "M. Matsuoka, et al" and insert -- M. Matsuoka, et al., --, therefor.

Title Page 2, in Item (56), under "OTHER PUBLICATIONS", in Column 1, Line 9, delete "Chen Shifu, et al" and insert -- Chen Shifu, et al., --, therefor.

Title Page 2, in Item (56), under "OTHER PUBLICATIONS", in Column 1, Line 16, delete "Q. Li, et al" and insert -- Q. Li, et al., --, therefor.

Title Page 2, in Item (56), under "OTHER PUBLICATIONS", in Column 1, Line 19, delete "Pinggui Wu, et al" and insert -- Pinggui Wu, et al., --, therefor.

Title Page 2, in Item (56), under "OTHER PUBLICATIONS", in Column 2, Line 10, delete "Akihiko Kudo, et al" and insert -- Akihiko Kudo, et al., --, therefor.

Signed and Sealed this  
Twelfth Day of November, 2013

Teresa Stanek Rea  
*Deputy Director of the United States Patent and Trademark Office*

Title Page 2, in Item (56), under "OTHER PUBLICATIONS", in Column 2, Line 13, delete "Hyun Woo Kang, et al" and insert -- Hyun Woo Kang, et al., --, therefor.

Title Page 2, in Item (56), under "OTHER PUBLICATIONS", in Column 2, Line 17, delete "Andrew Mills, et al" and insert -- Andrew Mills, et al., --, therefor.

Title Page 2, in Item (56), under "OTHER PUBLICATIONS", in Column 2, Line 20, delete "Nor Hafizah, et al" and insert -- Nor Hafizah, et al., --, therefor.

Title Page 2, in Item (56), under "OTHER PUBLICATIONS", in Column 2, Line 24, delete "Masaaki Kitano, et al" and insert -- Masaaki Kitano, et al., --, therefor.

In the Specification

In Column 4, Line 49, delete "Paz, Y. et al" and insert -- Paz, Y. et al., --, therefor.

In Column 4, Line 51, delete "Watanabe, T. et al," and insert -- Watanabe, T. et al., --, therefor.

In Column 4, Line 52, delete "entirties" and insert -- entireties --, therefor.

In Column 5, Line 63, delete "SnO2/TiO$_2$" and insert -- SnO$_2$/TiO$_2$ --, therefor.

In Column 11, Line 53, delete "130," and insert -- 130°, --, therefor.